(12) United States Patent
Leung

(10) Patent No.: US 12,092,180 B2
(45) Date of Patent: Sep. 17, 2024

(54) TORQUE LIMITING CONNECTOR

(71) Applicant: CareFusion 303, Inc., San Diego, CA (US)

(72) Inventor: Gilbert Leung, La Verne, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/449,201

(22) Filed: Aug. 14, 2023

(65) Prior Publication Data

US 2023/0392650 A1 Dec. 7, 2023

Related U.S. Application Data

(60) Continuation of application No. 17/941,998, filed on Sep. 9, 2022, now Pat. No. 11,767,886, which is a
(Continued)

(51) Int. Cl.
*F16D 7/04* (2006.01)
*A61M 39/10* (2006.01)

(52) U.S. Cl.
CPC ......... *F16D 7/048* (2013.01); *A61M 39/1011* (2013.01); *A61M 2039/1033* (2013.01); *A61M 2039/1044* (2013.01)

(58) Field of Classification Search
CPC .......... A61M 39/1011; A61M 39/1055; A61M 2039/1033; A61M 2039/1044; F16D 7/002; F16D 7/048; F16D 43/2028; F16L 37/18

(Continued)

(56) References Cited

U.S. PATENT DOCUMENTS 3,667,307 A 6/1972 Keich
4,480,736 A * 11/1984 Loizeau .............. F16F 15/1212
464/57

(Continued)

FOREIGN PATENT DOCUMENTS

CN 1128002 A 7/1996
CN 1849200 A 10/2006
(Continued)

OTHER PUBLICATIONS

Indian Examination Report in Application No. 202117041166 dated Dec. 12, 2022, 6 pages.
(Continued)

*Primary Examiner* — Josh Skroupa
(74) *Attorney, Agent, or Firm* — Morgan, Lewis & Bockius LLP

(57) ABSTRACT

A connector includes an outer connector, an inner connector, and a clutch that can collectively limit a torque transmitted through the connector, the outer connector can include a profile disposed on an inner surface thereof, and the inner connector may be disposed within the outer connector and can include an upper threaded portion and a lower threaded portion. The clutch can be disposed around and rotationally coupled to the inner connector and can include a plurality of clutch teeth extending from an outer surface of the clutch, wherein the plurality of clutch teeth are outwardly biased to be releasably engaged with the profile of the outer connector, and the plurality of clutch teeth can be configured to transfer torque from the outer connector to the inner connector when the torque is below a torque limit and prevent transfer of torque when the torque exceeds the torque limit.

20 Claims, 5 Drawing Sheets

Related U.S. Application Data division of application No. 16/287,913, filed on Feb. 27, 2019, now Pat. No. 11,441,611.

(58) Field of Classification Search
USPC .......................................................... 464/37
See application file for complete search history.

(56) References Cited

U.S. PATENT DOCUMENTS

| | | | |
|---|---|---|---|
| 4,570,769 | A | 2/1986 | Isaka |
| 5,020,648 | A | 6/1991 | Bush |
| 5,088,581 | A | 2/1992 | Duve |
| 5,242,154 | A * | 9/1993 | Schmidt ................ F16D 7/048 464/34 |
| 5,810,533 | A | 9/1998 | Nakamura |
| 6,234,904 | B1 | 5/2001 | Kawaguchi |
| 6,589,121 | B1 | 7/2003 | Leonard |
| 7,984,933 | B2 | 7/2011 | Helstern |
| 8,142,070 | B2 | 3/2012 | Bonnet |
| 8,256,699 | B2 * | 9/2012 | Ando ................ F16D 7/048 242/394.1 |
| 8,337,077 | B2 | 12/2012 | Giacobino |
| 8,888,143 | B2 * | 11/2014 | Fog ................ F16L 19/025 285/309 |
| 10,098,768 | B2 * | 10/2018 | Cummins ................ A61F 2/95 |
| 10,682,506 | B2 | 6/2020 | Iwakata |
| 11,441,611 | B2 * | 9/2022 | Leung ................ F16D 7/048 |
| 2002/0165053 | A1 | 11/2002 | Kimura |
| 2007/0254744 | A1 * | 11/2007 | Helstern ................ F16L 19/00 464/37 |
| 2009/0133980 | A1 | 5/2009 | Swaim et al. |
| 2013/0233053 | A1 | 9/2013 | Beemer et al. |
| 2018/0369559 | A1 | 12/2018 | Iwakata et al. |
| 2020/0121891 | A1 | 4/2020 | Zhang |

FOREIGN PATENT DOCUMENTS

| | | |
|---|---|---|
| CN | 101408233 A | 4/2009 |
| CN | 101432559 A | 5/2009 |
| CN | 109041571 A | 12/2018 |
| DE | 102007051263 A1 | 4/2009 |
| EP | 3415194 A1 | 12/2018 |
| WO | WO-2018161359 A1 | 9/2018 |
| WO | WO-2018189842 A | 10/2018 |

OTHER PUBLICATIONS

International Search Report and Written Opinion for Application No. PCT/US2020/019863, dated May 13, 2020, 14 pages.
Japanese Office Action for Application No. 2021-549959, dated Mar. 16, 2023, 5 pages.
Chinese Office Action for Application No. 202080016625.0, dated Jan. 11, 2024, 18 pages including translation.
Canadian Office Action for Application No. 3130306, dated Jun. 12, 2024, 5 pages.
Chinese Notification of Grant for Application No. 202080016625.0, dated May 9, 2024, 6 pages including translation.
Japanese Office Action for Application No. 2023-126812, dated Apr. 10, 2024, 4 pages including translation.

* cited by examiner

TORQUE LIMITING CONNECTOR

CROSS REFERENCE TO RELATED APPLICATIONS

This application is a continuation of U.S. patent application Ser. No. 17/941,998, entitled "TORQUE LIMITING CONNECTOR," filed on Sep. 9, 2022, which is a division of U.S. patent application Ser. No. 16/287,913, entitled "TORQUE LIMITING CONNECTOR," filed on Feb. 27, 2019, and granted as U.S. Pat. No. 11,441,611, the entirety of each of which is incorporated herein by reference for all purposes.

FIELD OF THE INVENTION

The present disclosure generally relates to connectors, and, in particular, to torque limiting connectors.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "W set," to a source of fluid, for example, an IV bag. Often, tubing, syringes, needles and other medical equipment are made with threaded connectors and/or a universal luer conical fitting that may be tightened to make it leak-free.

In some applications, overtightened connections may be difficult or impossible to remove by hand.

SUMMARY

The disclosed subject matter relates to infusion disposables. In certain embodiments, a torque limiting connector is disclosed that comprises an outer connector comprising a profile disposed on an inner surface of the outer connector; an inner connector disposed within the outer connector, the inner connector comprising: an upper threaded portion; and a lower threaded portion; and a clutch disposed around and rotationally coupled to the inner connector, the clutch comprising a plurality of clutch teeth extending from an outer surface of the clutch, wherein the plurality of clutch teeth are outwardly biased to be releasably engaged with the profile of the outer connector, wherein the plurality of clutch teeth are configured to transfer an operational torque from the outer connector to the inner connector when the operational torque is below a torque limit, and the plurality of clutch teeth are forced inward to disengage the profile of the outer connector and prevent transfer of the operational torque when the operational torque exceeds the torque limit.

In certain embodiments, a torque limiting connector is disclosed that comprises an outer connector comprising a profile disposed on an inner surface of the outer connector; an inner connector disposed within the outer connector, the inner connector comprising: an upper threaded portion; and a lower threaded portion; and a clutch disposed around and rotationally coupled to the inner connector, the clutch comprising a plurality of clutch teeth extending from an outer surface of the clutch, wherein the plurality of clutch teeth are outwardly biased to be releasably engaged with the profile of the outer connector, wherein the plurality of clutch teeth are configured to permit the outer connector to rotate the inner connector when an operational torque is below a torque limit, and the plurality of clutch teeth are forced inward to disengage the profile of the outer connector and permit rotation of the outer connector relative to the inner connector when the operational torque exceeds the torque limit.

In certain embodiments, a method to tighten a connection is disclosed that comprises threadedly engaging a first connector with a second connector; rotating an outer connector of the first connector at an operational torque below a connection torque limit; and rotating an inner connector of the first connector via the rotation of the outer connector, wherein a clutch rotationally engages the inner connector and the outer connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed torque limiting connector incorporates a two-part connector with a clutch. The clutch can be disposed between the inner connector and the outer connector to limit torque to the inner connector. By limiting torque to the inner connector, overtightening of connectors can be prevented, preventing damage to connectors and simplifying removal.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the connection of medical fittings for the administration of medical fluid using the disclosed torque limiting connector, it is to be understood that this description is only an example of usage and does not limit the scope of the claims. Various aspects of the disclosed torque limiting connector may be used in any application where it is desirable to provide for the connection of various tubing and fittings without overtightening.

The disclosed torque limiting connector overcomes several challenges discovered with respect to certain conventional connectors. One challenge with certain conventional connectors is that threaded connectors may be easily overtightened if the engagement surfaces are wet, such as from a disinfectant. Further, clinicians may overtighten conventional connectors to prevent leaks. Because overtightened connectors may require increased (up to three times greater) disconnection force, necessitating the use of mechanical aids such as forceps or pliers, or the replacement of the connected catheter and/or tubing sets, the use of conventional connectors is undesirable.

Therefore, in accordance with the present disclosure, it is advantageous to provide a torque limiting connector as described herein that eliminates or substantially reduces potential overtightening of the connector. The disclosed torque limiting connector provides an intermediate clutch that permits tightening of the connector, while preventing overtightening of the connector.

An example of a torque limiting connector that prevents overtightening is now described.

Figure 1:
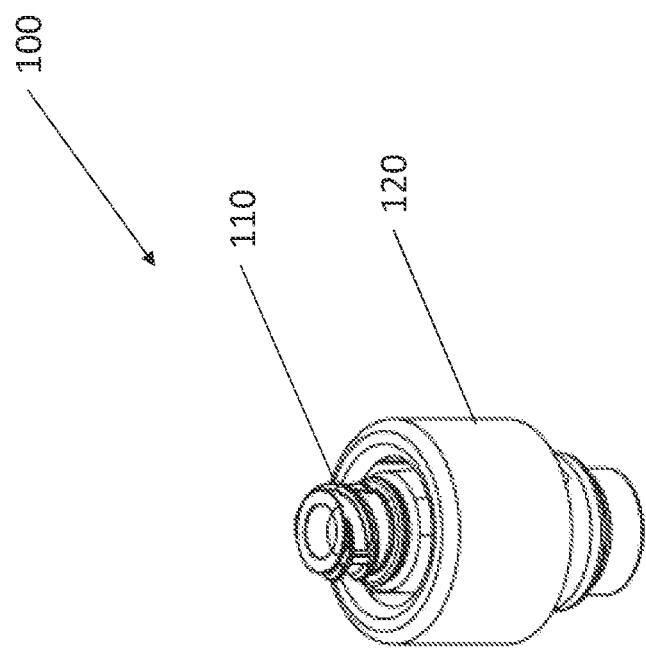
FIG. 1 is a perspective view of a connector assembly, in accordance with various aspects of the present disclosure.
Figure 2:
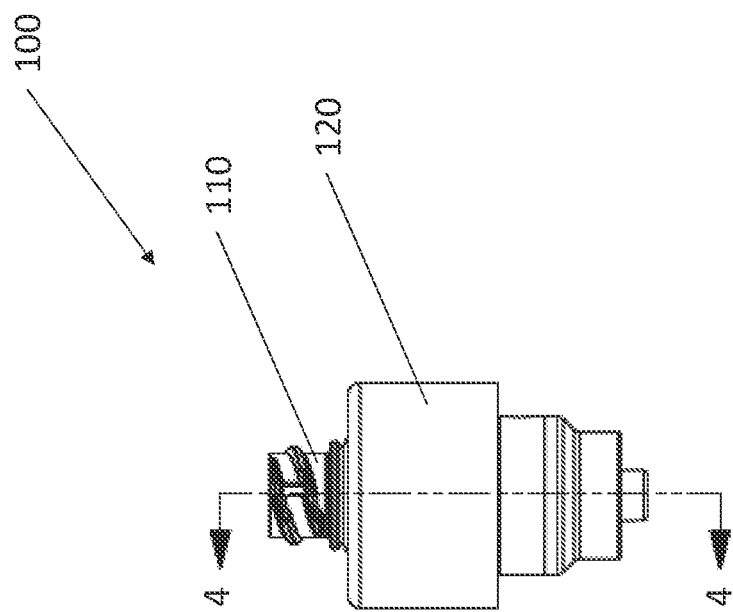
FIG. 2 is an elevation view of the connector assembly of FIG. 1, in accordance with various aspects of the present disclosure.

FIG. 1 is a perspective view of a connector assembly 100, in accordance with various aspects of the present disclosure. FIG. 2 is an elevation view of the connector assembly 100 of FIG. 1, in accordance with various aspects of the present disclosure. With reference to FIGS. 1 and 2, the connector assembly 100 facilitates a fluid connection with a mating connector. In the depicted example, the inner connector 110 can be threaded to a mating connector at the upper end and/or the lower end. For example, the connector assembly 100 can be utilized with medical tubing.

To tighten the connector assembly 100 to a mating connector, the outer connector 120 can be twisted to tighten the threaded connections of the inner connector 110. In some applications, a desired tightness or torque is specified for the connection between the connector assembly 100 and the mating connector. However, during use, clinicians may overtighten connections. For example, the disconnecting force for a connection may be higher after disinfecting the connectors. Mating connections may be disassembled or removed by twisting the connector assembly 100 in the opposite direction.

Advantageously, the connector assembly 100 prevents the inner connector 110 from being overtightened to a mating connector. During operation, until the desired torque is reached, rotation of the outer connector 120 rotates the inner connector 110, tightening the mating connection therebetween.

However, after the desired torque is reached, a clutch mechanism prevents the outer connector 120 from further tightening the inner connector 110. Therefore, after the desired torque is reached, the outer connector 120 may be rotated independently of the inner connector 110.

In addition to preventing overtightening of the inner connector 110, the connector assembly 100 can provide feedback or signals to the user that the desired mating torque has been reached. For example, upon rotation of the outer connector 120 after a desired torque is reached, the connector assembly 100 may provide an auditory or tactile signal or feedback (such as a "click").

Figure 3:
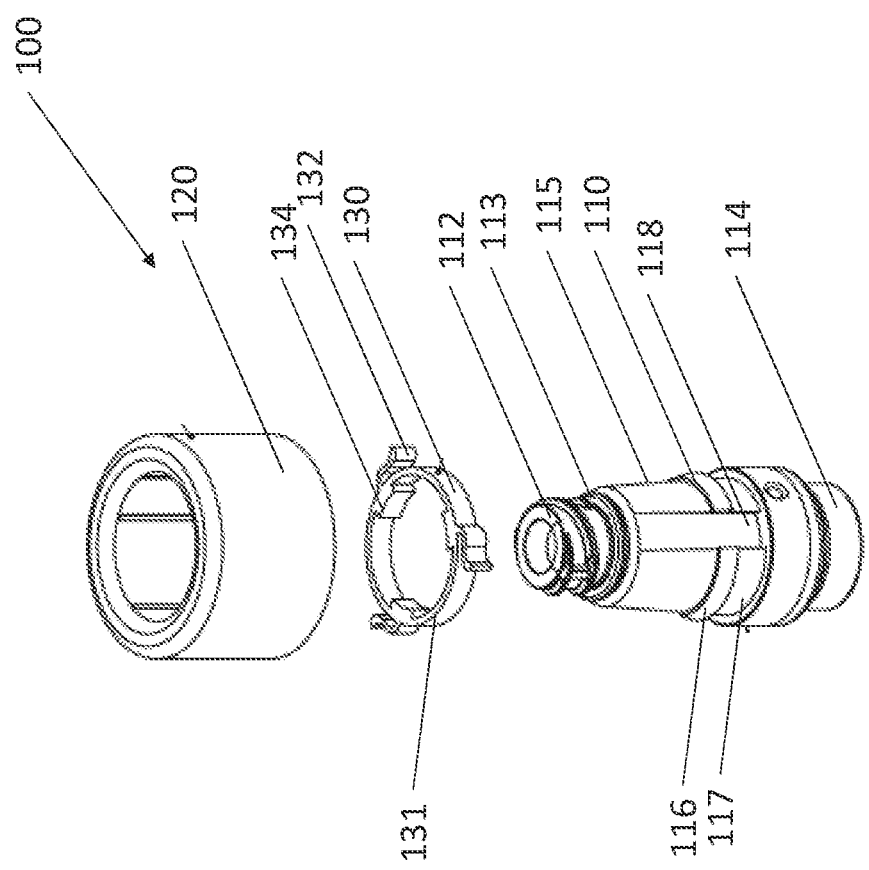
FIG. 3 is an exploded perspective view of the connector assembly of FIG. 1, in accordance with various aspects of the present disclosure.
Figure 4:
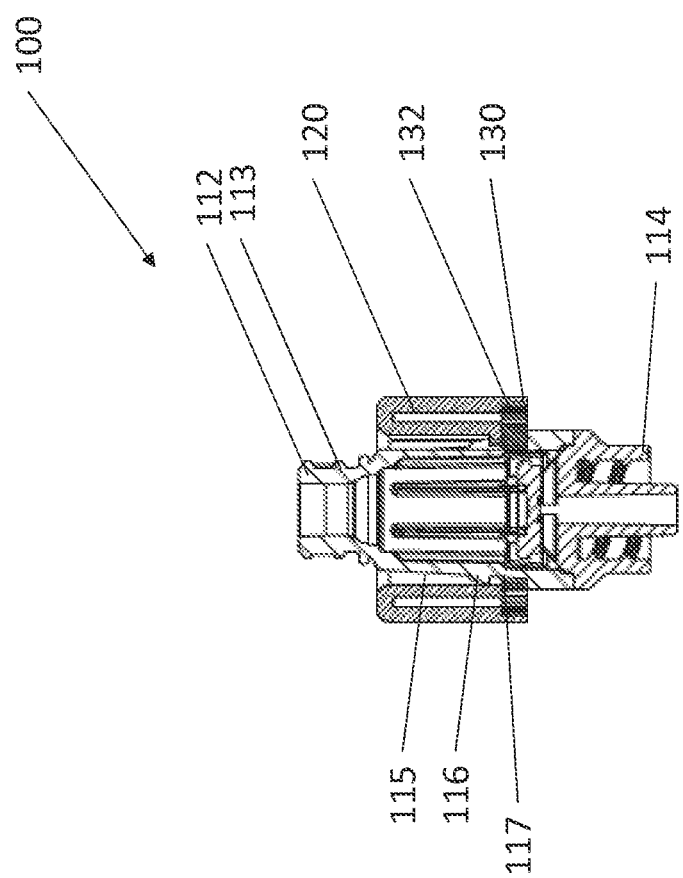
FIG. 4 is a cross-sectional view of the connector assembly of FIG. 1, in accordance with various aspects of the present disclosure.

FIG. 3 is an exploded perspective view of the connector assembly of FIG. 1, in accordance with various aspects of the present disclosure. FIG. 4 is a cross-sectional view of the connector assembly of FIG. 1, in accordance with various aspects of the present disclosure. With reference to FIGS. 3 and 4, a clutch 130 permits the connector assembly 100 to limit the amount of torque delivered to the inner connector 110 from the outer connector 120.

In the depicted example, the clutch 130 is rotatably coupled with the inner connector 110 and releasably engaged with the outer connector 120. Therefore, during operation, the clutch 130 allows the outer connector 120 to rotate the inner connector 110 until a desired maximum torque is achieved.

As shown, the clutch 130 may be disposed between the inner connector 110 and the outer connector 120. In some embodiments, the clutch 130 is concentrically disposed about the inner connector 110. For example, the clutch 130 can be disposed along the tapered outer surface 115 of the inner connector 110. Optionally, the clutch 130 can be axially retained relative to the inner connector 110. For example, the clutch 130 can be axially retained in a clutch groove 117 defined by an angled flange 116 formed on the tapered outer surface 115 of the inner connector 110. In some embodiments, the outer connector 120 can include features to axially retain the clutch 130. The angled flange 116 can have an angled surface to facilitate assembly of the clutch 130 onto the inner connector 110.

In the depicted example, the clutch 130 can receive rotational torque from the outer connector 120. Further, as illustrated, the clutch teeth 132 extend from an outer surface 131 of the clutch 130 to interface with an inner profile of the outer connector 120. The interface of the clutch teeth 132 with the outer connector 120 allows for torque to be transferred to the clutch 130.

As illustrated, the outer connector 120 is disposed about the inner connector 110 and the clutch 130. Optionally, the outer connector 120 is concentrically disposed about the inner connector 110 and the clutch 130. In some embodiments, the outer connector 120 is axially retained relative to the inner connector 110. For example, the outer connector 120 can snap fit over the angled flange 116 of the inner connector 110 to axially retain the outer connector 120 relative to the inner connector 110.

During operation, to transfer torque from the clutch 130 to the inner connector 110, the clutch 130 is rotationally coupled with the inner connector 110 to permit the clutch 130 and the inner connector 110 to rotate together. In the depicted example, the clutch 130 transfers rotational torque to the inner connector 110 via dogs or features 134 formed on the inner surface of the clutch 130 that engage with the outer surface of the inner connector 110. In some embodiments, the features 134 of the clutch 130 engage with the slots or channels 118 formed in the tapered outer surface 115 of the inner connector 110. Therefore, during operation, torque from the outer connector 120 is transferred to the inner connector 110 via the clutch 130 to rotate the inner connector 110 relative to any mating connectors.

In the depicted example, the inner connector 110 includes an upper threaded portion 112 and a lower threaded portion 114. By rotating the inner connector 110, the upper threaded portion 112 and/or the lower threaded portion 114 can be tightened. For example, the threaded surface 113 of the upper threaded portion 112 can be tightened into a mating connector at a desired torque or until the upper threaded portion 112 bottoms out against the mating connector. Similarly, the lower threaded portion 114 can be tightened into a mating connector at a desired torque or until the lower threaded portion 114 bottoms out against the mating connector. As previously described, the outer connector 120 can rotate the inner connector 110 until the predetermined maximum torque is achieved.

During operation, after the maximum torque is achieved, the clutch teeth 132 can disengage from the outer connector 120, permitting the outer connector 120 to spin without tightening the inner connector 110. In some embodiments, the number of clutch teeth 132 in engagement with the outer connector 120 can determine the maximum torque that can be imparted from the outer connector 120 to the inner connector 110 prior to disengaging the outer connector 120. For example, the clutch 130 can include more clutch teeth 132 to allow the outer connector 120 to impart more torque to the inner connector 110, while in some embodiments, the clutch 130 can include fewer clutch teeth 132 to allow the outer connector 120 to impart less torque to the inner connector 110. By way of example, the clutch 130 can include one clutch tooth 132, three clutch teeth 132, five clutch teeth 132, or any other suitable number of clutch teeth 132.

Similarly, the clutch 130 can permit the outer connector 120 to loosen the inner connector 110 from any mating connectors. The clutch 130 and the outer connector 120 may interface to limit loosening torque.

Figure 6:
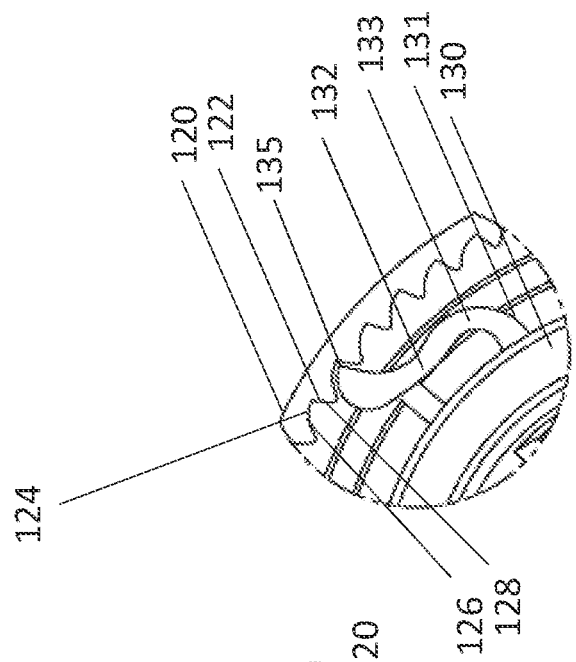
FIG. 6 is a detail view of the connector assembly of FIG. 5, in accordance with various aspects of the present disclosure.
Figure 5:
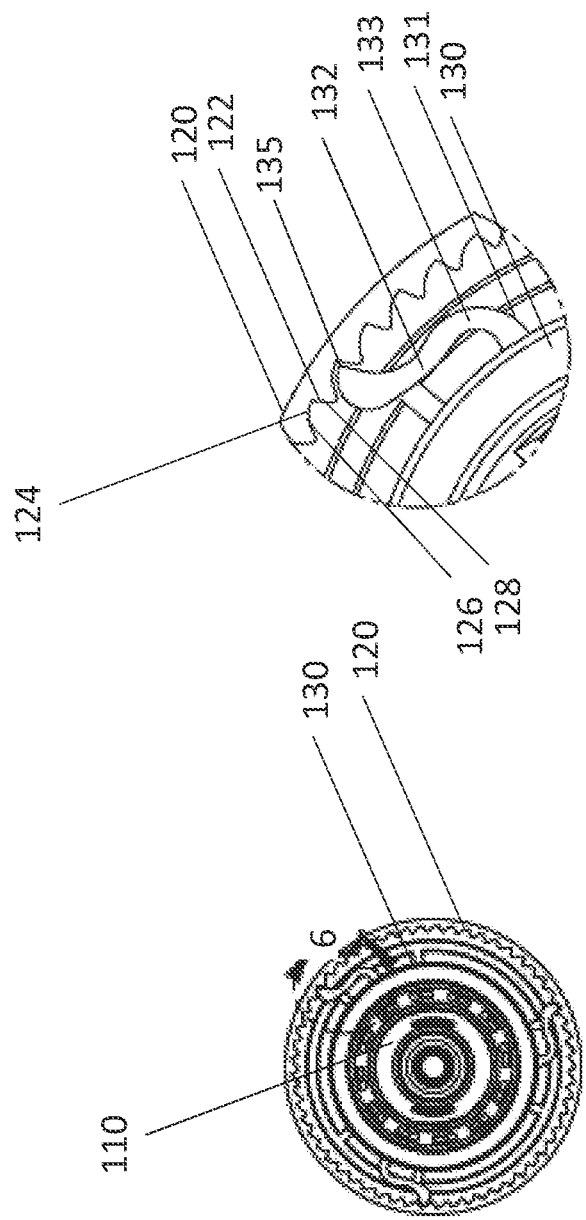
FIG. 5 is a bottom view of the connector assembly of FIG. 1, in accordance with various aspects of the present disclosure.

FIG. 5 is a bottom view of the connector assembly of FIG. 1, in accordance with various aspects of the present disclosure. FIG. 6 is a detail view of the connector assembly of FIG. 5, in accordance with various aspects of the present disclosure. With reference to FIGS. 5 and 6, clutch teeth 132 releasably engage against the connector profile 122 of the outer connector 120 to receive or transfer torque from the outer connector 120.

During operation, the outer connector 120 is rotated, thereby rotating the connector profile 122. The rotation of the connector profile 122 transmits torque to the clutch teeth 132 and thereby to the inner connector 110. The outer connector 120 can continue to provide torque to or otherwise rotate the inner connector 110 as long as the clutch teeth 132 remain in engagement with the connector profile 122.

In the depicted example, the clutch teeth 132 extend radially outward toward the connector profile 122. As shown, the clutch teeth 132 are outwardly biased to maintain engagement with the connector profile 122. In some embodiments, the clutch teeth 132 are resiliently or elastically biased toward the connector profile 122. In some applications, the biasing force of the clutch teeth 132 can be modified by selecting the material, thickness, depth, and other characteristics of the clutch teeth 132 and the clutch 130. Optionally, the angle or geometry of the bend 133 of the clutch teeth 132 can be modified to adjust the biasing force of the clutch teeth.

As illustrated, the connector profile 122 includes a plurality of engagement features 124 that can transfer rotational force from the outer connector 120 to the engaged clutch teeth 132 in a tangent direction to provide torque to the inner connector 110 and/or force in a radial direction to urge the clutch teeth 132 inwardly and out of engagement with the connector profile 122. For example, an engagement feature 124 that transfers rotational force from the outer connector 120 to a clutch tooth 132 in a primarily tangential direction (the engagement feature 124 extending primarily normal to the outer connector 120) will transfer proportionally more torque than inward radial force to a clutch tooth 132 compared to an engagement feature 124 that transfers rotational force from the outer connector 120 to the clutch tooth 132 in a primarily radial direction (the engagement feature 124 extending primarily tangent to the outer connector 120), which may transfer less torque and more inward radial force to the clutch tooth 132. In some embodiments, the engagement features 124 can include a combination tangent and radial components to control the proportion of torque that is transferred from the outer connector 120 to the inner connector 110 and the amount of inward radial force that is applied to the clutch teeth 132.

During operation, when the inward radial force imparted on the clutch teeth 132 by the engagement features 124 overcomes the outward biasing force maintaining the clutch teeth 132 in engagement with the connector profile 122, the clutch teeth 132 are disengaged from the outer connector 120 and allow the outer connector 120 to rotate relative to the inner connector 110, limiting torque transferred to the inner connector 110. Optionally, the disengaged clutch teeth 132 may provide an audible and/or tactile signal to the user.

By modifying geometric and material properties of the engagement features 124 and the clutch teeth 132, the amount of torque that is applied to the inner connector 110 prior to disengaging the clutch teeth 132 can be controlled. For example, the relative angle of the engagement features 124 can be adjusted to have a higher operational torque limit or a lower operational torque limit.

In some embodiments, the connector assembly 100 can provide different torque limits for tightening and loosening. For example, the connector assembly 100 may provide a lower torque limit for tightening the connector assembly 100 and a higher torque limit for loosening the connector assembly 100.

In the depicted example, the engagement features 124 may be asymmetric. As shown, the profile on the leading side 126 of the engagement feature 124 may differ from the profile on the trailing side 128 of the engagement feature 124. In some embodiments, the leading side 126 may allow for less torque to be imparted in the tightening direction (the leading side 126 extending relatively tangent to the outer connector 120) while the trailing side 128 may allow for greater torque to be imparted in the loosening direction (the trailing side 128 extending relatively normal to the outer connector 120).

Optionally, the engagement features 124 can include varying geometric features. For example, the engagement features 124 can be rounded or angular to facilitate or inhibit the clutch teeth 132 to disengaging from the connector profile 122. Similarly, complimentary geometric features of the tooth profile 135 of the clutch tooth 132 can be altered to engage with the engagement features 124.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A torque limiting connector, comprising:
   an inner connector comprising an upper threaded portion, a lower threaded portion, and a flange extending radially outward in direction away from an outer surface of the inner connector;
   a clutch rotationally coupled with the inner connector and axially aligned between the lower threaded portion and the flange, the clutch comprising a plurality of outwardly biased clutch teeth extending from an outer surface of the clutch; and
   an outer connector concentrically disposed about the inner connector and the clutch, and snap fit over the flange to axially retain the outer connector relative to the inner connector, the outer connector comprising an inner surface having a profile releasably engaged by the outwardly biased clutch teeth;
   wherein the plurality of clutch teeth is configured to transfer an operational torque from the outer connector to the inner connector when the operational torque is below a torque limit, and the plurality of clutch teeth are forced inward to disengage the profile of the outer connector and resist transfer of the operational torque from the outer connector to the inner connector when the operational torque exceeds the torque limit.

2. The torque limiting connector of claim 1, wherein the outer surface of the inner connector comprises a channel, and the clutch comprises an inner surface having a coupling feature configured to engage against the channel.

3. The torque limiting connector of claim 1, wherein the outer surface of the inner connector is tapered such that a cross-sectional width of the inner connector decreases in a direction from the lower threaded portion toward the upper threaded portion.

4. The torque limiting connector of claim 1, wherein the clutch is concentrically disposed about the inner connector.

5. The torque limiting connector of claim 1, wherein the plurality of clutch teeth comprises three clutch teeth.

6. The torque limiting connector of claim 1, wherein the profile comprises a plurality of engagement features.

7. The torque limiting connector of claim 6, wherein each of the plurality of engagement features is asymmetric.

8. The torque limiting connector of claim 7, wherein each of the plurality of engagement features comprises a leading side and a trailing side, wherein the leading side comprises a rounded geometry and the trailing side comprises an angular geometry.

9. The torque limiting connector of claim 6, wherein a tooth of the plurality of clutch teeth comprises a convex surface configured to engage against a leading side of each of the plurality of engagement features.

10. The torque limiting connector of claim 6, wherein a tooth of the plurality of clutch teeth comprises a concave surface configured to engage against a trailing side of each of the plurality of engagement features.

11. The torque limiting connector of claim 1, wherein the clutch and the outer connector emit an audible signal when the operational torque exceeds the torque limit.

12. The torque limiting connector of claim 1, wherein the clutch and the outer connector emit a tactile signal when the operational torque exceeds the torque limit.

13. The torque limiting connector of claim 1, wherein the outer surface of the inner connector comprises a channel that extends through the flange.

14. A method of providing a torque limiting connector, the method comprising:
providing an inner connector comprising an upper threaded portion, a lower threaded portion, and a flange extending radially outward in direction away from an outer surface of the inner connector;
providing a clutch rotationally coupled with the outer surface of the inner connector, and axially aligned between the lower threaded portion and the flange; and
providing an outer connector concentrically disposed about the inner connector and the clutch, and snap fit over the flange to axially retain the outer connector relative to the inner connector, wherein a plurality of outwardly biased clutch teeth extending from an outer surface of the clutch are releasably engaged against an inner surface of the outer connector having a profile;
wherein the plurality of clutch teeth is configured to transfer an operational torque from the outer connector to the inner connector when the operational torque is below a torque limit, and to bias radially inward toward the inner connector to disengage the profile of the outer connector and prevent transfer of the operational torque when the operational torque exceeds the torque limit.

15. The method of claim 14, wherein providing the clutch rotationally coupled with the outer surface of the inner connector comprises inserting the inner connector through the clutch in a direction from the upper threaded portion toward the lower threaded portion, such that the clutch is concentrically disposed about the inner connector.

16. The method of claim 14, wherein providing the outer connector concentrically disposed about the inner connector and the clutch comprises moving the outer connector over the clutch in a direction from the upper threaded portion toward the lower threaded portion, such that the outer connector is concentrically disposed about the clutch and the inner connector.

17. The method of claim 14, wherein providing the clutch rotationally coupled with the outer surface of the inner connector comprises inserting the inner connector through the clutch in a direction from the upper threaded portion toward the lower threaded portion until the clutch is positioned between the flange of the inner connector and the lower threaded portion of the inner connector.

18. The method of claim 14, wherein providing the outer connector concentrically disposed about the inner connector and the clutch comprises inserting the inner connector through the outer connector until the outer connector is snap fit over the flange.

19. The method of claim 14, wherein providing the outer connector concentrically disposed about the inner connector and the clutch comprises aligning the plurality of clutch teeth with a plurality of engagement features of the profile.

20. The method of claim 14, wherein providing the outer connector concentrically disposed about the inner connector and the clutch comprises biasing the plurality of clutch teeth radially inward toward the inner connector.

* * * * *